(12) United States Patent
Pedrozo et al.

(10) Patent No.: US 7,595,062 B2
(45) Date of Patent: Sep. 29, 2009

(54) JOINT RESURFACING ORTHOPAEDIC IMPLANT AND ASSOCIATED METHOD

(75) Inventors: Hugo A. Pedrozo, Silver Lake, IN (US); Matthew N. Widmer, Genoa, OH (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 11/192,222

(22) Filed: Jul. 28, 2005

(65) Prior Publication Data

US 2007/0026053 A1 Feb. 1, 2007

(51) Int. Cl.
A61F 2/00 (2006.01)
C07K 14/00 (2006.01)
(52) U.S. Cl. ............... 424/422; 623/11.11; 514/2
(58) Field of Classification Search ............... None
See application file for complete search history.

(56) References Cited

U.S. PATENT DOCUMENTS

| | | |
|---|---|---|
| 3,272,204 A | 9/1966 | Artandi et al. |
| 3,562,820 A | 2/1971 | Braun |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,352,463 A | 10/1982 | Baker |
| 4,400,833 A | 8/1983 | Kurland |
| 4,418,691 A | 12/1983 | Yannas et al. |
| 4,610,397 A | 9/1986 | Fischer et al. |
| 4,642,120 A | 2/1987 | Nevo et al. |
| 4,669,473 A | 6/1987 | Richards et al. |
| 4,703,108 A | 10/1987 | Silver et al. |
| 4,705,040 A | 11/1987 | Mueller et al. |
| 4,741,330 A | 5/1988 | Hayhurst |
| 4,750,492 A | 6/1988 | Jacobs |
| 4,846,835 A | 7/1989 | Grande |
| 4,873,976 A | 10/1989 | Schreiber |
| 4,880,429 A | 11/1989 | Stone |
| 4,902,508 A | 2/1990 | Badylak et al. |
| 4,919,667 A | 4/1990 | Richmond |
| 4,956,178 A | 9/1990 | Badylak et al. |
| 4,956,179 A | 9/1990 | Bamberg et al. |
| 4,976,715 A | 12/1990 | Bays et al. |
| 5,007,934 A | 4/1991 | Stone |
| 5,061,286 A | 10/1991 | Lyle |
| 5,102,421 A | 4/1992 | Anspach, Jr. |
| 5,108,438 A | 4/1992 | Stone |
| 5,128,326 A | 7/1992 | Balazs et al. |
| RE34,021 E | 8/1992 | Mueller et al. |
| 5,236,431 A | 8/1993 | Gogolewski et al. |
| 5,246,441 A | 9/1993 | Ross et al. |
| 5,258,015 A | 11/1993 | Li et al. |
| 5,269,809 A | 12/1993 | Hayhurst et al. |
| 5,275,826 A | 1/1994 | Badylak et al. |
| 5,281,422 A | 1/1994 | Badylak et al. |
| 5,306,311 A | 4/1994 | Stone et al. |
| 5,320,633 A | 6/1994 | Allen et al. |
| 5,329,846 A | 7/1994 | Bonutti |
| 5,350,583 A | 9/1994 | Yoshizato et al. |
| 5,352,463 A | 10/1994 | Badylak et al. |
| 5,372,821 A | 12/1994 | Badylak et al. |
| 5,374,268 A | 12/1994 | Sander |
| 5,376,118 A | 12/1994 | Kaplan et al. |
| 5,380,334 A | 1/1995 | Torrier et al. |
| 5,445,833 A | 8/1995 | Badylak et al. |
| 5,447,940 A | 9/1995 | Harvey et al. |
| 5,460,962 A | 10/1995 | Kemp |
| 5,464,929 A | 11/1995 | Bezwada et al. |
| 5,479,033 A | 12/1995 | Baca et al. |
| 5,514,181 A | 5/1996 | Light et al. |
| 5,516,533 A | 5/1996 | Badylak et al. |
| 5,520,691 A | 5/1996 | Branch |
| 5,545,178 A | 8/1996 | Kensey et al. |
| 5,554,389 A | 9/1996 | Badylak et al. |
| 5,569,252 A | 10/1996 | Justin et al. |
| 5,573,784 A | 11/1996 | Badylak et al. |
| 5,591,234 A | 1/1997 | Kirsch |
| 5,593,441 A | 1/1997 | Lichtenstein et al. |
| 5,595,621 A | 1/1997 | Light et al. |
| 5,595,751 A | 1/1997 | Bezwada et al. |
| 5,597,579 A | 1/1997 | Bezwada et al. |

(Continued)

FOREIGN PATENT DOCUMENTS

| | | |
|---|---|---|
| EP | 0 446 105 A2 | 1/1992 |
| EP | 0 591 991 A2 | 4/1994 |
| EP | 0 632 999 A1 | 11/1995 |
| EP | 0 734 736 A1 | 10/1996 |
| EP | 1070487 | 1/2001 |
| EP | 1593400 A1 | 11/2005 |
| FR | 2422386 | 4/1978 |

(Continued)

OTHER PUBLICATIONS

Adams and Watt, "Regulation of development and differentiation by the extracellular matrix", Development 117: 1183-1198 (1993).*
Bierbaum et al., "Collageneous matrix coating on titanium implants modified with decorin and chondroitin sulfate: characterization and influence on osteoblastic cells", J Biomed Mater Res 77A: 551-562 (2006).*
Chang et al., "Hyaluronan inhibits osteoclast differentiation via toll-like receptor 4", Journal of Cell Science 120: 166-176 (2007).*
Ledet et al., "A pilot study to evaluate the effectiveness of small intestinal submucosa used to repair spinal ligaments in the goat", The Spine Journal 2: 188-196 (2002).*

(Continued)

Primary Examiner—Anand U Desai
(74) Attorney, Agent, or Firm—Barnes & Thornburg LLP (57) ABSTRACT

An orthopaedic implant includes a porous structure made of a type I collagen matrix having at least one sheet of a naturally occurring extracellular matrix secured thereto. Methods of making and using such an implant are also disclosed.

18 Claims, 5 Drawing Sheets

U.S. PATENT DOCUMENTS

| | | |
|---|---|---|
| 5,601,558 A | 2/1997 | Torrie et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,626,614 A | 5/1997 | Hart |
| 5,630,824 A | 5/1997 | Hart |
| 5,632,745 A | 5/1997 | Schwartz |
| 5,641,518 A | 6/1997 | Badylak et al. |
| 5,645,850 A | 7/1997 | Bezwada et al. |
| 5,645,860 A | 7/1997 | Knapp, Jr. et al. |
| 5,648,088 A | 7/1997 | Bezwada et al. |
| 5,660,225 A | 8/1997 | Saffran |
| 5,668,288 A | 9/1997 | Storey et al. |
| 5,669,912 A | 9/1997 | Spetzler |
| 5,677,355 A | 10/1997 | Shalaby et al. |
| 5,681,353 A | 10/1997 | Li et al. |
| 5,693,085 A | 12/1997 | Buirge et al. |
| 5,695,998 A | 12/1997 | Badylak et al. |
| 5,698,213 A | 12/1997 | Jamiolkowski et al. |
| 5,700,583 A | 12/1997 | Jamiolkowski et al. |
| 5,702,462 A | 12/1997 | Oberlander |
| 5,711,960 A | 1/1998 | Shikinami |
| 5,711,969 A | 1/1998 | Patel et al. |
| 5,725,556 A | 3/1998 | Moser et al. |
| 5,730,933 A | 3/1998 | Peterson |
| 5,733,337 A | 3/1998 | Carr, Jr. et al. |
| 5,733,868 A | 3/1998 | Peterson et al. |
| 5,735,897 A | 4/1998 | Buirge |
| 5,735,903 A | 4/1998 | Li et al. |
| 5,736,372 A | 4/1998 | Vacanti et al. |
| 5,753,267 A | 5/1998 | Badylak et al. |
| 5,755,791 A | 5/1998 | Whitson et al. |
| 5,759,190 A | 6/1998 | Vibe-Hansen et al. |
| 5,759,205 A | 6/1998 | Valentini |
| 5,759,208 A | 6/1998 | Valentini |
| 5,762,600 A | 6/1998 | Bruchman et al. |
| 5,762,966 A | 6/1998 | Knapp et al. |
| 5,769,899 A | 6/1998 | Schwartz et al. |
| 5,773,577 A | 6/1998 | Cappello |
| 5,788,625 A | 8/1998 | Plouhar et al. |
| 5,795,353 A | 8/1998 | Felt |
| 5,800,537 A | 9/1998 | Bell |
| 5,830,708 A | 11/1998 | Naughton |
| 5,834,232 A | 11/1998 | Bishop et al. |
| 5,842,477 A | 12/1998 | Naughton et al. |
| 5,847,012 A | 12/1998 | Shalaby et al. |
| 5,855,610 A | 1/1999 | Vacanti et al. |
| 5,855,613 A | 1/1999 | Antanavich et al. |
| 5,855,619 A | 1/1999 | Caplan et al. |
| 5,859,150 A | 1/1999 | Jamiolkowski et al. |
| 5,861,004 A | 1/1999 | Kensey et al. |
| 5,863,551 A | 1/1999 | Woerly |
| 5,866,414 A | 2/1999 | Badylak et al. |
| 5,885,619 A | 3/1999 | Patel et al. |
| 5,891,558 A | 4/1999 | Bell et al. |
| 5,899,939 A | 5/1999 | Boyce et al. |
| 5,906,997 A | 5/1999 | Schwartz et al. |
| 5,916,265 A | 6/1999 | Hu |
| 5,922,028 A | 7/1999 | Plouhar et al. |
| 5,939,323 A | 8/1999 | Valentini et al. |
| 5,954,723 A | 9/1999 | Spetzler |
| 5,954,747 A | 9/1999 | Clark |
| 5,955,110 A | 9/1999 | Patel et al. |
| 5,958,874 A | 9/1999 | Clark et al. |
| 5,968,096 A | 10/1999 | Whitson et al. |
| 5,971,987 A | 10/1999 | Huxel et al. |
| 5,980,524 A | 11/1999 | Justin et al. |
| 5,981,802 A | 11/1999 | Katz |
| 5,981,825 A | 11/1999 | Brekke |
| 5,989,269 A | 11/1999 | Vibe-Hansen et al. |
| 5,989,280 A | 11/1999 | Euteneuer et al. |
| 5,993,475 A | 11/1999 | Lin et al. |
| 5,993,844 A | 11/1999 | Abraham et al. |
| 5,997,575 A | 12/1999 | Whitson et al. |
| 6,010,525 A | 1/2000 | Bonutti et al. |
| 6,017,301 A | 1/2000 | Schwartz et al. |
| 6,017,348 A | 1/2000 | Hart et al. |
| 6,027,744 A | 2/2000 | Vacanti et al. |
| 6,034,140 A | 3/2000 | Schwartz et al. |
| 6,042,610 A | 3/2000 | Li et al. |
| 6,051,750 A | 4/2000 | Bell |
| 6,056,752 A | 5/2000 | Roger |
| 6,056,777 A | 5/2000 | McDowell |
| 6,056,778 A | 5/2000 | Grafton et al. |
| 6,060,640 A | 5/2000 | Pauley et al. |
| 6,066,160 A | 5/2000 | Colvin et al. |
| 6,068,648 A | 5/2000 | Cole et al. |
| 6,077,989 A | 6/2000 | Kandel et al. |
| 6,080,194 A | 6/2000 | Pachence et al. |
| 6,093,201 A | 7/2000 | Cooper et al. |
| 6,096,347 A | 8/2000 | Jaeger et al. |
| 6,099,567 A | 8/2000 | Badylak et al. |
| 6,110,212 A | 8/2000 | Gregory |
| 6,126,686 A | 10/2000 | Badylak et al. |
| 6,133,325 A | 10/2000 | Schwartz et al. |
| 6,146,385 A | 11/2000 | Torrie et al. |
| 6,152,935 A | 11/2000 | Kammerer et al. |
| 6,153,292 A | 11/2000 | Bell et al. |
| 6,156,044 A | 12/2000 | Kammerer et al. |
| 6,165,225 A | 12/2000 | Antanavich et al. |
| 6,171,344 B1 | 1/2001 | Atala |
| 6,176,880 B1 | 1/2001 | Plouhar et al. |
| 6,179,840 B1 | 1/2001 | Bowman |
| 6,179,872 B1 | 1/2001 | Bell et al. |
| 6,187,039 B1 | 2/2001 | Hiles et al. |
| 6,197,296 B1 | 3/2001 | Davies et al. |
| 6,206,931 B1 | 3/2001 | Cook et al. |
| 6,214,048 B1 | 4/2001 | Ito et al. |
| 6,214,049 B1 | 4/2001 | Gayer et al. |
| 6,224,892 B1 | 5/2001 | Searle |
| 6,235,057 B1 | 5/2001 | Roger et al. |
| 6,242,247 B1 | 6/2001 | Rieser et al. |
| 6,251,143 B1 | 6/2001 | Schwartz et al. |
| 6,251,876 B1 | 6/2001 | Bellini et al. |
| 6,258,124 B1 | 7/2001 | Darois et al. |
| 6,264,702 B1 | 7/2001 | Ory et al. |
| 6,265,333 B1 | 7/2001 | Dzenis et al. |
| 6,267,957 B1 | 7/2001 | Green et al. |
| 6,270,530 B1 | 8/2001 | Eldridge et al. |
| 6,273,893 B1 | 8/2001 | McAllen, III et al. |
| 6,280,473 B1 | 8/2001 | Lemperle et al. |
| 6,280,474 B1 | 8/2001 | Cassidy et al. |
| 6,283,980 B1 | 9/2001 | Vibe-Hansen et al. |
| 6,288,043 B1 | 9/2001 | Spiro et al. |
| 6,290,711 B1 | 9/2001 | Caspari et al. |
| 6,293,961 B2 | 9/2001 | Schwartz et al. |
| 6,294,041 B1 | 9/2001 | Boyce et al. |
| 6,299,905 B1 | 10/2001 | Peterson et al. |
| 6,306,156 B1 | 10/2001 | Clark |
| 6,306,159 B1 | 10/2001 | Schwartz et al. |
| 6,306,177 B1 | 10/2001 | Felt et al. |
| 6,319,258 B1 | 11/2001 | McAllen, III et al. |
| 6,319,271 B1 | 11/2001 | Schwartz et al. |
| 6,326,025 B1 | 12/2001 | Sigler et al. |
| 6,333,029 B1 | 12/2001 | Vyakarnam et al. |
| 6,334,872 B1 | 1/2002 | Termin et al. |
| 6,355,699 B1 | 3/2002 | Vyakarnam et al. |
| 6,358,284 B1 | 3/2002 | Fearnot et al. |
| 6,364,884 B1 | 4/2002 | Bowman et al. |
| 6,371,958 B1 | 4/2002 | Overaker |
| 6,373,221 B1 | 4/2002 | Koike et al. |
| 6,379,367 B1 | 4/2002 | Vibe-Hansen et al. |
| 6,379,710 B1 | 4/2002 | Badylak |
| 6,383,221 B1 | 5/2002 | Scarborough et al. |

| | | |
|---|---|---|
| 6,387,693 B2 | 5/2002 | Rieser et al. |
| 6,402,766 B2 | 6/2002 | Bowman et al. |
| 6,409,764 B1 | 6/2002 | White et al. |
| 6,423,073 B2 | 7/2002 | Bowman |
| 6,436,110 B2 | 8/2002 | Bowman et al. |
| 6,440,444 B2 | 8/2002 | Boyce et al. |
| 6,447,517 B1 | 9/2002 | Bowman |
| 6,451,032 B1 | 9/2002 | Ory et al. |
| 6,458,158 B1 | 10/2002 | Anderson et al. |
| 6,458,383 B2 | 10/2002 | Chen et al. |
| 6,464,729 B1 | 10/2002 | Kandel |
| 6,497,650 B1 | 12/2002 | Nicolo |
| 6,497,707 B1 | 12/2002 | Bowman et al. |
| 6,508,821 B1 | 1/2003 | Schwartz et al. |
| 6,517,564 B1 | 2/2003 | Grafton et al. |
| 6,566,345 B2 | 5/2003 | Miller et al. |
| 6,572,650 B1 | 6/2003 | Abraham et al. |
| 6,592,623 B1 | 7/2003 | Bowlin et al. |
| 6,638,312 B2 | 10/2003 | Plouhar et al. |
| 6,652,872 B2 | 11/2003 | Nevo et al. |
| 6,666,892 B2 | 12/2003 | Hiles et al. |
| 6,692,499 B2 | 2/2004 | Törmäläet et al. |
| 6,812,221 B2 | 11/2004 | McKeehan et al. |
| 6,840,962 B1 | 1/2005 | Vacanti et al. |
| 6,869,938 B1 | 3/2005 | Schwartz et al. |
| 6,989,034 B2 | 1/2006 | Hammer et al. |
| 7,201,917 B2 * | 4/2007 | Malaviya et al. ............ 424/423 |
| 7,217,294 B2 * | 5/2007 | Kusanagi et al. ......... 623/18.11 |
| 7,354,627 B2 * | 4/2008 | Pedrozo et al. ............. 427/487 |
| 2001/0002446 A1 | 5/2001 | Plouhar et al. |
| 2001/0023373 A1 | 9/2001 | Plouhar et al. |
| 2001/0024658 A1 | 9/2001 | Chen et al. |
| 2001/0043943 A1 | 11/2001 | Coffey |
| 2002/0019649 A1 | 2/2002 | Sikora et al. |
| 2002/0031551 A1 | 3/2002 | Peterson et al. |
| 2002/0034533 A1 | 3/2002 | Peterson et al. |
| 2002/0038151 A1 | 3/2002 | Plouhar et al. |
| 2002/0048595 A1 | 4/2002 | Geistlich et al. |
| 2002/0052628 A1 | 5/2002 | Bowman |
| 2002/0090725 A1 | 7/2002 | Simpson et al. |
| 2002/0091444 A1 | 7/2002 | Yang |
| 2002/0095157 A1 | 7/2002 | Bowman |
| 2002/0099448 A1 | 7/2002 | Hiles |
| 2002/0165611 A1 | 11/2002 | Enzerink et al. |
| 2002/0169465 A1 | 11/2002 | Bowman et al. |
| 2002/0173806 A1 | 11/2002 | Giannetti et al. |
| 2003/0014126 A1 | 1/2003 | Patel et al. |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0044444 A1 | 3/2003 | Malaviya et al. |
| 2003/0049299 A1 | 3/2003 | Malaviya et al. |
| 2003/0078617 A1 | 4/2003 | Schwartz et al. |
| 2003/0212447 A1 | 11/2003 | Euteneuer et al. |
| 2004/0059431 A1 | 3/2004 | Plouhar et al. |
| 2004/0143344 A1 | 7/2004 | Malaviya et al. |
| 2004/0166169 A1 | 8/2004 | Malaviya et al. |
| 2004/0220574 A1 | 11/2004 | Pelo et al. |
| 2005/0027307 A1 | 2/2005 | Schwartz |
| 2005/0249771 A1 | 11/2005 | Malaviya et al. |
| 2005/0249772 A1 | 11/2005 | Malaviya et al. |

FOREIGN PATENT DOCUMENTS

| | | |
|---|---|---|
| GB | 2 215 209 | 9/1989 |
| JP | 11319068 A | 11/1999 |
| WO | WO 90/09769 | 9/1990 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | WO 95/32623 | 12/1995 |
| WO | WO96/24304 | 8/1996 |
| WO | WO 96/24661 | 8/1996 |
| WO | WO 97/05193 | 2/1997 |
| WO | WO 97/37613 | 10/1997 |
| WO | WO 98/06445 | 2/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 98/40111 | 9/1998 |
| WO | WO 99/03979 | 1/1999 |
| WO | WO 99/43786 | 9/1999 |
| WO | WO 99/47188 | 9/1999 |
| WO | WO 00/15765 | 3/2000 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 01/70293 A1 | 9/2001 |
| WO | WO 02/22184 | 3/2002 |
| WO | WO 03/007784 | 1/2003 |
| WO | WO 03/007788 A2 | 1/2003 |
| WO | WO 03/007790 A2 | 1/2003 |

OTHER PUBLICATIONS

Hiles et al., "Mechanical properties of xenogeneic small-intestinal submucosa when used as an aortic graft in the dog", *Journal of Biomedical Materials Research*, vol. 29, 883-891, (1995).

Sandusky, et al., "Healing Comparison of Small Intestine Submucosa and ePTFE Grafts in the Canine Carotid Artery", *J. Surg.Res.*, 58:415-420, (1995).

Knapp, et al., "Biocompatibility of Small-Intestine Submucosa in Urinary Tract as Augmentation Cystoplasty Graft and Injectable Suspension", *J Endourology*, 8:125-130, (1994).

Kropp et al., "Regenerative Bladder Augmentation: A Review of the Initial Preclinical Studies with Porcine Small Intestinal Submucosa", *Muscle, Matrix, and Bladder Function*. Plenum Press, New York, (1995).

Kropp et al., "Experimental Assessment of Small Intestinal Submucosa as a Bladder Wall Substitute", *Urology* 446:396-400, (1995).

Vaught et al., "Detrusor Regeneration in the Rat Using Porcine Small Intestinal Submucosa Grafts: Functional Innervation and Receptor Expression", *J. Urol.*, 155:374-378, (1996).

Kropp et al, Characterization of Small Intestinal Submucosa Regenerated Canine Detrusor: Assessment of Reinnervation, In Vitro Compliance and contractility, *J. of Urol*,156:599-607, (1996).

Kropp et al., "Regenerative Urinary Bladder Augmentation Using Small Intestinal Submucosa: Urodynamic and Histopathologic Assessment in Long-Term Canine Bladder Augmentations", *Journal of Urology*, 155:2098-2104, (1996).

Aiken et al, "Small Intestinal Submucosa as an Intra-Articular Ligamentous Graft Material: A Pilot Study in Dogs", *Vet Comp Orthopedics Traumatology*, 7:124-128, (1994).

Badylak et al., "The Use of Xenogeneic Small Intestinal Submucosa as a Biomaterial for Achille's Tendon Repair in a dog model", *J Biomed Materials*, 29:977-985, (1995).

Hodde et al., "The Effect of Range of Motion Upon Remodeling of Small Intestinal Submucosa (SIS) when used as an Achilles Tendon Repair Material in the Rabbit", *Tissue Engineering* 3, 1:27-37, (1997).

Ferrand et al., "Directional Porosity of Porcine Small-Intestinal Submucosa", *J Biomed Materials Res*, 27:1235-1241, (1993).

Hiles et al., "Porosity of Porcine Small-Intestinal Submucosa for use as a Vascular Graft", *J Biomed Materials Res*, 27: 139-144, (1993).

Hodde et al., "Glycosaminoglycan Content of Small Intestinal Submucosa: A Bioscaffold for Tissue Replacement", *Tissue Engineering*, 2:3, 209-217, (1996).

Prevel et al., "Small Intestinal Submucosa: Utilization for Repair of Rodent Abdominal Wall Defects", *Ann Plast Surg*, 35:374-380, (1995).

Clarke et al., "Intestine Submucosa and Polypropylene Mesh for Abdominal Wall Repair in Dogs", *J Surg Res*, 60:107-114, (1996).

Prevel et al., "Small Intestinal Submucosa: Utilization as a Wound Dressing in Full-Thickness Rodent Wounds", *Ann Plast Surg*. 35:381-388, (1995).

Cobb et al., "Histology after Dural Grafting with Small Intestinal Submucosa", *Surgical Neurology*, 46: 389- 394, (1996).

Cobb et al., "Porcine Small Intestinal Submucosa as a Dural Substitute", *Surgical Neurology*, 51:99-104, (1999).

Voytik-Harbin et al., "Application and Evaluation of the AlamarBlue Assay for Cell Growth and Survival of Fibroblasts", *Journal of Immunological Methods*, In Vitro *Cell Bio-Animal*, 34: 2399-246, (1998).

Suckow, M.A., "Enhanced Bone Regeneration Using Porcine Small Intestinal Submucosa", *J. Invest Surg*, 12: 277, (1999).

Badylak , S., et al., "Naturally Occurring Extracellular Matrix as a Scaffold for Musculoskeletal Repair", *Clin Orthop*, 3675:S333-S3433, (1999).

Cook, J.L. et al., "Induction of Meniscal Regeneration in Dogs Using a Novel Biomaterial", *Am J Sports Med*, 27: 658, (1999).

Dejardin, L.M. et al., "Use of small intestinal submucosal implants for regeneration of large fascial defects: an experimental study in dogs", *J Biomed Mater Res*, 46:203-211, (1999).

Sacks, M.S., et al., "Quantification of the fiber architecture and biaxial mechanical behavior of porcine intestinal submucosa", *J Biomed Mater Res*, 46:1-10, (1999).

COOK® News Releases, "COOK® Introduces Innovative Surgisis™ Soft Tissue Repair Biomaterial", (May 21, 2000).

COOK® News Releases, "COOK® Oasis™ Wound Dressing Biomaterial From COOK® Remodels Partial Thickness Skin Injuries", (Dec. 23, 1999).

COOK® News Releases, "Cook Incorporated Forms Dedicated Tissue Engineered Products Group", (Feb. 16, 2000).

COOK® News Releases, "FDA Clears Oasis™ Wound Dressing Biomaterial From COOK® For Full-Thickness Skin Injuries", (Jan. 24, 2000).

Klootwyk, et al., "The Use of Xenographic SIS as a Biomaterial for Achilles Tendon Repair in Dogs," *First SIS Symposium*, Dec. 1996, USA.

Lenz, et al., "SIS as an ACL Replacement in Dogs and Goats," *First Symposium*, Dec. 1996, USA.

Cook, et al., "Comparison of SIS Cancellous Bone as Substrates for Three-Dimensional Culture of Canine Articular Chondrocytes," *First SIS Symposium*, Dec. 1996, USA.

Badylak, et al., "Different Configurations of Small Intestinal Submucosa as a Biomaterial for Achilles Tendon Repair in a Dog Model," *First SIS Symposium*, Dec. 1996, USA.

Voytik-Harbin & Badylak, "Induction of Osteogenic Activity By Small Intestinal Submucosa in Rat Calvaria Non-union Defects," *First SIS Symposium*, Dec. 1996, USA.

Kandel, et al., "SIS and Reconstituted Cartilage and Its Use in Joint Resurfacing of Focal Defects in Rabbits," *First SIS Symposium*, Dec. 1996, USA.

Tullius, et al., "Differential Permeabilty of SIS," *First SIS Symposium*, Dec. 1996, USA.

Obermiller, et al., "Suture Retention Strength of SIS," *First SIS Symposium*, Dec. 1996, USA.

Shelton, et al., "Repair of the Canine Medial Meniscus using SIS: A Feasibility Study," *Second SIS Symposium*, Dec. 1998, USA.

Cook, et al., "Meniscal Regeneration in dogs Using Grafts of SIS," *Second SIS Symposium*, Dec. 1998, USA.

Welch, et al., "Healing of Canine Meniscal Defect with Small Intestinal Submucosa Implants," Dec. 1998, USA.

Solchaga, et al., "SIS as Delivery Vehicle for Mesenchymal Progenitor Cells," Dec. 1998, USA.

Paulino, et al., "The Use of an SIS-PGA Composite Graft for Repair of Cartilage Defect," Dec. 1998, USA.

Toombs and May, "Clinical Follow-Up of Three Canine ACL Reconstructions Using an SIS ACL Device," Dec. 1998, USA.

Tomasek and Gifford, "Small Intestinal Submucosa Matrix Regulates The Differentiation of Myofibroblasts," *Third SIS Symposium*, Nov. 2000, USA.

Cook, et al., "Tissue Engineering for Meniscal Repair Using SIS," *Third SIS Symposium*, Nov. 2000, USA.

Lifrak, et al., "Enhanced Repair of Goat Meniscal Defects Using Porcine Small Intestinal Submucosa (SIS)," *Third SIS Symposium*, Nov. 2000, USA.

Hoffman, "SIS Disc Replacement For the Temporomandibular Joint," *Third SIS Symposium*, Nov. 2000, USA.

Kaeding, "Use of SIS In The Surgical Treatment of Chronic Symptomatic Patella Tendinosis," *Third SIS Symposium*, Nov. 2000, USA.

Tomczak and Kaeding, "Use of SIS in The Surgical Treatment of Tendinosis About The Foot And Ankle," *Third SIS Symposium*, Nov. 2000, USA.

Moore, et al., "Bridging Segmental Defects In Long Bones With Intramedullary Tubes And Periosteal Sleeves Made From Small Intestinal Submucosa (SIS)," *Third SIS Symposium*, Nov. 2000, USA.

Wang, et al., "Small Intestinal Submucosa Enhances Healing of Medical Collateral Ligament In A Rabbit Model," *Third SIS Symposium*, Nov. 2000, USA.

Ojha, et al., "PGA-PIIa Versus Small Intestinal Submucosa (SIS): A Comparison of Neo-Cartilage Grown From Two Scaffold Materials," *Third SIS Symposium*, Nov. 2000, USA.

Wiklerson, "Use of The Porcine Small Intestine Submucosal Tissue Graft And Repair of Rotator Cuff Tears," *Third SIS Symposium*, Nov. 2000, USA.

"Small Intestinal Submucosa," *Third SIS Symposium*, Nov. 2000, USA.

"Current Clinical Applications of SIS," *Third SIS Symposium*, Nov. 2000, USA.

Hodde, et al., "Glycosaminoglycan Content of Small Intestinal Submucosa: A Potential for GAG-Growth Interactions in SIS-Mediated Healing", *First Symposium*, Dec. 1996, USA.

Friess, "Collagen in drug delivery and tissue engineering",*Advanced Drug Delivery Reviews*, vol. 55, No. 12, 2003, pp. 1529-1530.

Olsen et al., "Recombinant collagen and gelatin for drug delivery", *Advanced Drug Delivery Reviews*, vol. 55, No. 12, 2003, pp. 1547-1567.

Aigner et al., "Collagens—major component of the physiological cartilage matrix, major target of cartilage degeneration, major tool in cartilage repair", *Advanced Drug Delivery Reviews*, vol. 55, No. 12, 2003, pp. 1569-1593.

Geiger et al., "Collagen sponges for bone regeneration with rhBMP-2", *Advanced Drug Delivery Reviews*, vol. 55, No. 12, 2003, pp. 1613-1629.

Ruszczak et al., "Collagen as a carrier for on-site delivery of antibacterial drugs", *Advanced Drug Delivery Reviews*, vol. 55, No. 12, 2003, pp. 1679-1698.

O'Grady et al., "Global regulatory registration requirements for collagen-based combination products: points to consider", *Advanced Drug Delivery Reviews*, vol. 55, No. 12, 2003, pp. 1699-1721.

Matthews et al., "Electrospinning of Collagen Type II: A Feasibility Study", *Journal of Bioactive and Compatible Polymers*, vol. 18, Mar. 2003, pp. 125-134.

Biscarini et al., "Growth of High Vacuum Sublimed Oligomer Thin Films", *ACS Polymer Preprints*, vol. 37, No. 2, 1996, pp. 618-619.

Biscarini et al., "Morphology and roughness of high-vacuum sublimed oligomer thin films", *Thin Solid Films*, vol. 439-443, 1996, pp. 284-285.

Biscarini et al., "Scaling Behavior of Anisotropic Organic Thin Films Grown in High-Vacuum", *Physical Review Letters*, vol. 78, No. 12, Mar. 24, 1997, pp. 2389-2392.

Voytik-Harbin et al., "Identification of Extractable Growth Factors from Small Intestinal Submucosa", *Journal of Cellular Biochemistry*, vol. 67, 1997, pp. 478-491.

McPherson, Ph.D. et al., "Characterization of Fibronectin Derived from Porcine Small Intestinal Submucosa", *Tissue Engineering*, vol. 4, No. 1, 1998, pp. 75-83.

Hodde, et al., "Vascular Endothelial Growth Factor in Porcine-Derived Extracellular Matrix", *Endothelium*, vol. 8(1), 2001, pp. 11-24.

Hodde et al., "Wounds: A Compendium of Clinical Research and Practice", Website: :www.hmpcommunications.com/WNDS, Printed: Jul. 12, 2005, 7 pgs.

Hurst et al., "Mapping of the distribution of significant proteins and proteoglycans in small intestinal submucosa by fluorescence microscopy", *J. Biomater. Sci. Polymer Edn*., vol. 12, No. 11, 2001, pp. 1267-1279.

Hodde et al., "Fibronectin peptides mediate HMEC adhesion to porcine-derived extracellular matrix", *Biomaterials*, vol. 23, 2002, pp. 1841-1848.

Hodde, "Naturally Occurring Scaffolds for Soft Tissue Repair and Regeneration", *Tissue Engineering*, vol. 8, No. 2, 2002, pp. 295-308.

Allman et al., Xenogeneic Extracellular Matrix Grafts Elicit a Th2-Restricted Immune Response, *Transplantation*, vol. 71, No. 11, Jun. 15, 2001, pp. 1631-1640.

Allman et al., "The Th2-Restricted Immune Response to Xenogeneic Small Intestinal Submucosa Does Not Influence Systemic Protective Immunity to Viral and Bacterial Pathogens", *Tissue Engineering*, vol. 8, No. 1, 2002, pp. 53-62.

Salem et al., "Interactions of 3T3 fibroblasts and endothelial with defined pore ffeatures", *J. Biomed Materials Res*., vol. 61, No. 2, 2002, pp. 212-217.

Definitions of "intertwine" and "twine" , *American Heritage Dictionary of the English Language Online*, Accessed Sep. 29, 2005, 2 pgs.

How to Cut Meat Products 2001, *Urschel Corp*., Accessed online at fr.urschel.com/literature/HTCMeat.pdf on Oct. 3, 2005, 8 pgs.

Definitions of "comminute" and "slurry", *Dictionary.com*; Accessed Sep. 20, 2005, 2 pgs.

Hodde and Hiles, "Bioactive FGF-2 in sterilized extracellular matrix", Wounds, 13(5): 195-201 (2001).

O'Meara, Patrick, "The basic science of meniscus repair," Orthopaedic review, Jun. 1993, pp. 681-686.

Clearfix screw advertisement, 1998, Innovasive devices, Inc.

Winters and Justin, "Clearflx meniscal screw", Innovasive devices, Inc. 1998.

Surgical dynamics, meniscal stapler advertisement, 1997.

Bionix implants, Meniscus arrow advertisement, 1996.

Instrument makar, inc., Meniscus mender II, 1989.

William G. Clancy, Jr., M.D., and Ben K. Graf, M.D., "Arthroscopic Meniscal Repair," ACUFEX Microsurigal Inc., advertisement, 1988.

P. K. Chu et al., "Plasma-surface modification of biomaterials", Materials Science and Engineering, Reports: A Review Journal, vol. 36, No. 5-6, Mar. 29, 2002, pp. 143-206.

Arnoczky et al., The microvasculature of the meniscus and its response to injury—An experimental study in the dog, *Am. J. Sports Med*., 1983, 11(3); pp. 131-141.

Fox et al., Trephination of incomplete meniscal tears, *Arthroscopy*, 1993, 9(4); pp. 451-455.

Arnoczky et al., Meniscal repair using an exogenous fibrin clot—An experimental study of dogs, *J. Bone Joint Surg. Am*., 1988, 70(8), pp. 1209-1216.

Rodeo, "Arthroscopic meniscal repair with use of the outside-in technique", *Instr. Course Lect*., 2000, 49, pp. 195-206.

Stollsteimer et al., "Meniscal allograft transplantation: a 1- to 5-year follow-up of 22 patients", *Arhroscopy*, 2000, 16(4), pp. 343-347.

Rodeo, "Meniscal allografts—where do we stand?", *Am. J. Sports Med*., 2001, 29(2), pp. 246-261.

Sweigart et al., "Toward tissue engineering of the knee meniscus", *Tissue Eng*., 2001, 7(2), pp. 111-129.

Boss et al., "Technical innovative: creation of a peripheral vascularized trough to enhance healing in cryopreserved meniscal allograft reconstruction", *Knee Surg Sports Traumatol Arthrosc*., 2000, 8(3), pgs.

J.S. Pieper et al "Preparation and characterization of porous crosslinked collagenous matrices containing bioavailable chondroitin suplhate" Biomateriais 1999, 20: 847-858.

P.B. van Wachem et al. "In vivo biocompatability of carbodiimide-crosslinked collagen matrices: Effects of crosslink density, heparin immobilization, and bFGF loading" J. Biomed. Mater. Res. 2001, 55 (3): 368-378.

Kyumin Whang "A biodegradable polymer scaffold for delivery of osteotroplc factors" Biomaterials 2000, 21 (24): 2545-2551.

J.S. Pieper et al. Attachment of glycosaminoglycans to collangenous matrices modulates the tissue response in rats, Biomaterials 2000, 21(16): 1689-1699.

Kristen Billiar et al. "Effects of carbodiimide crosslinking conditions on the physical properties of laminated intestinal submucosa", J. Biomed. Mater. Res. 2001, 51(1): 101-108.

Toshimitsu Momose et al. "Surface modification of extrasynovial tendon by chemically modified hyaluronic acid coating" J. Biomed. Mater. Res. 2002, 59: 219-224.

Handbook of Biodegradable Polymers Hardwood Press 1997 (251-272).

Cohn et al., "Biodegradable PEO/PLA block copolymers," Journal of Biomedical Materials Research, 1988, 22 (993-1009).

"Polymer Preprints" (ACS Division of Polymer Chemistry), 1989. 30 (1): 498.

The Encyclopedia of Polymer Science, 1988 (13) 31-41.

"Handbook of Biodegradable Polymers" Hardwood Press 1977 (161-182).

"Handbook of Biodegradable Polymers" Hardwood Press 1997 (99-118).

Disilvestro et al., "Effects of Cross-Linking on the Mechanical Properties of a Porous Foam Scaffold of Small Intestine Submucosa", Society for Biomaterials 29th Annual Meeting Transactions, 2003, pp. 88.

Ide et al., "Collagen Hybridization with Poly(I-Lactic Acid) Braid Promotes Ligament Cell Migration", Mater. Sci. Eng. C, 17(1-2), 95-99 (2001).

Bercovy et al., "Carbon-PGLA Prosthesis for Ligament Reconstruction Experimental Basis and Short Term Results in Man", Clin. Orthop. Relat. Res., (196), 159-68 (1985).

Zhu et al, "Immobilization of Biomacromolecules onto Aminolyzed Poly(L-lactic acid) toward Acceleration of Endothelium Regeneration", Tissue Engineering, v 10, pp. 53-61, 2004.

Cheng & Teoh, "Surface modification of ultra thin poly (ÿ caprolactone) films using acrylic acid and collagen", Biomaterials, v25(11), pp. 1991-2001, 2004.

Wan et al., "Cell adhesion on gaseous plasma modified poly-(L-lactide) surface under shear stress field", Biomaterials, v24(21), pp. 3757-3764, 2003.

Yang et al., "Effect of surface treatment on the biocompatibility of microbial polyhydroxyalkanoates", Biomaterials, v 23 (5), pp. 1391-1397, 2002.

Croll et al., "Controllable surface modification of Poly(lactic-co-glycolic acid) (PLGA) by hydrolysis or aminolysis I: physical, chemical, and theoretical aspects", Biomacromolecules, Mar.-Apr. 2004, 5(2): 463-473.

Kwon et al., "Fibroblast culture on surface-modified poly (glycolide-co- ÿ-caprolactone) scaffold for soft tissue regeneration", J. Biomater Sci Polym ed. 2001, 12(10) 1147-60.

Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, February; 17(2): 151-159.

Tan W, Krishnaraj R, Desai TA "Evaluation of nanostructured composite collagen-chitosan matrices for tissue engineering", Tissue Eng Apr; 7(2): 203-210, 2001.

Arnoczky SP "Building a meniscus", Biological considerations, Clin Orthop Oct; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18(11), pp. 33-39, 2003.

Zhang et al., Design of nanostructured biological materials through self-assembly of peptides and proteins, MIT Current Opinion in chemical Biology, 2002, 6:865-871.

Krčma, "Nonwoven Textiles", *Textile Trade Press*, Manchester, England, 1962, 6 pgs.

Answers.com,. Definition of "freeze-dry", Accessed on May 12, 2005, 6 pgs.

Ma et al., "Microtubular architecture of biodegradable polymer scaffolds", *J. Biomed. Materials Res.*, vol. 56, No. 4, 2001, pp. 469-477.

Ma et al., "Biodegradable Polymer Scaffolds with Well-Defined Interconnected Spherical Pore Network", *Tissue Engineering*, vol. 7, No. 1, 2001, pp. 23-33.

Klawitter et al., "An Evaluation of Bone Growth into Porous High Density Polyethylene", *J. Biomed. Materials Res.*, vol. 10, (1976) pp. 311-323.

White et al., "Biomaterial Aspects of Interpore-200 Porous Hydroxyapatite", *Dental Clinics of North America*, Reconstructive Implant Surgery and Implant Prosthodontics 1, vol. 30, No. 1, pp. 49-67, (1986).

Shors, Coralline Bone Graft Substitutes, *Orthopaedic Clinics of North America*, Bone Grafting and Bone Graft Substitutes, vol. 30, No. 4, Oct. 1999, pp. 599-613.

Wang, Experimental Study of Osteogenic Activity of Sintered Hydroxyapatite—On the Relationship of Sintering Temperature and Pore Size—, *J. Jpn. Orthop. Assoc.*, vol. 64, 1990, pp. 847-859.

Nehrer et al., "Matrix collagen type and pore size influence behavior of seeded canine chondrocytes", *Biomaterials*, vol. 18, No. 11, 1997, pp. 769-776.

Siegel et al., "Meniscal allografts", *Clin Sports Med.*, 1993, 12(1), pp. 59-80.

Klompmaker et al., "Meniscal replacement using a porous polymer prosthesis: a preliminary study in the dog.", *Biomaterials*, 1996, 17(12), pp. 1169-1175.

de Groot et al., "Use of porous polyurethanes for meniscal reconstruction and meniscal protheses", *Biomaterials*, 1996, 17(2), pp. 163-173.

Spaans et al., "Solvent-free fabrication of micro-porous polyurethane amide and polyurethane-urea scaffolds for repair and replacement of the knee-joint meniscus", *Biomaterials*, 2000, 21(23), pp. 2453-2460.

Stone et al., "Regeneration of meniscal cartilage with use of a collagen scaffold—Analysis of Preliminary data", *J. Bone Joint Surg. Am.*, 1997, 79(12), pp. 1770-1777.

Rodkey et al., "A clinical study of collagen meniscus implants to restore the injured meniscus", *Clin. Orthop.*, 1999, 49(367 Suppl.), pp. S281-S292.

Merriam-Webster Online Dictionary definitions of "suspension", "suspend", "cohesive", "cohesion", "comminute", "pulverize", "submucosa", and "tissue". Accessed Mar. 30, 2006, 9 pgs.

Resin Technology Group, LLC, "Viscosity chart", ://www.resintechgroup.com/tables/viscosity.html, accessed online Mar. 30, 2006, 1 pg.

Definitions from Onelook.com for "trimethylen" and "trimethylene", (downloaded Mar. 17, 2006).

Supplementary European Search Report, Appln No. 02753403.1 (PCT/US 223190) dated Dec. 21, 2006 (3 pages).

Definitions of "intertwine" and "twine." American Heritage Dictionary of the English Language Online. Accessed Sep. 29, 2005. 2 pages.

On-line Medical Dictionary definition of "extracellular matrix" located at //cancerweb.ncl.ac.uk/cgibin/omd? extracellular+matrix, (Nov. 18, 1997).

* cited by examiner

JOINT RESURFACING ORTHOPAEDIC IMPLANT AND ASSOCIATED METHOD

FIELD OF THE DISCLOSURE

The present disclosure relates generally to orthopaedic implants and methods of using the same.

BACKGROUND

During the lifetime of a patient, it may be necessary to perform an orthopaedic procedure, such as a joint replacement procedure, on the patient as a result of, for example, disease or trauma. The orthopaedic procedure may involve the use of an implant, such as a patch, which is implanted onto the articulating surface of a patient's joint.

SUMMARY

According to one aspect of the present disclosure, an orthopaedic implant includes a porous structure made of a type I collagen matrix having at least one sheet of a naturally occurring extracellular matrix secured thereto.

The type I collagen matrix may be extracted from a naturally occurring extracellular matrix. In certain embodiments, at least 75% of the collagen fibers of the matrix have an α-helical tertiary structure. In certain embodiments, the porous structure is self-assembled.

In certain embodiments, the porous structure is sandwiched between a number of sheets of a naturally occurring extracellular matrix. In certain embodiments a plurality of sheets of a naturally occurring extracellular matrix is positioned on each side of the porous structure. A binding solution containing type I collagen may be disposed between adjacent sheets of the naturally occurring extracellular matrix.

The sheets of naturally occurring extracellular matrix may be sheets of SIS.

A bioactive agent may be incorporated into the implant.

The implant may be formed to include a number of protrusions on one side with a corresponding number of indentations on the other side. The implant may be so formed by use of a die.

According to another aspect of the disclosure, an orthopaedic device includes a resorbable implant configured to resurface a joint. The implant has a number of indentations on a first surface thereof. The implant may have a corresponding number of protrusions on a second, opposite surface thereof.

The resorbable implant may be made of a naturally occurring extracellular matrix material.

The construct may include a porous structure having a collagen type I matrix.

In certain embodiments, one or more sheets of a naturally occurring extracellular matrix may be secured to the porous structure.

A bioactive agent may be incorporated into the implant.

According to yet another aspect, a method of making an orthopaedic implant includes extracting collagen type I fibers from a naturally occurring extracellular matrix and inducing self assembly of the fibers to form a porous structure. At least one sheet of a naturally occurring extracellular matrix may be secured to the porous structure.

In certain embodiments, at least 75% of the self assembled collagen fibers have an α-helical tertiary structure. In certain embodiments, the porous structure is self-assembled.

In certain embodiments, the porous structure is sandwiched between a number of sheets of a naturally occurring extracellular matrix. In certain embodiments a plurality of sheets of naturally occurring extracellular matrix is positioned on each side of the porous structure. A binding solution containing type I collagen may be disposed between adjacent sheets of the naturally occurring extracellular matrix.

The sheets of naturally occurring extracellular matrix may be sheets of SIS.

A bioactive agent may be incorporated into the implant.

The implant may be formed to include a number of indentations on one side thereof. The implant may be formed to include a corresponding number of protrusions on the other side. The implant may be so formed by use of a die.

According to another aspect of the disclosure, a method of making an orthopaedic implant includes operating a work tool to form a plurality of indentations in a resorbable orthopaedic implant.

The resorbable implant may include a naturally occurring extracellular matrix.

The implant may include a porous structure having a collagen type I matrix.

In certain embodiments, one or more sheets of a naturally occurring extracellular matrix may be secured to the porous structure.

A bioactive agent may be incorporated into the implant.

In another aspect of the disclosure, a method of performing a surgical joint procedure includes positioning a resorbable orthopaedic implant on a joint surface. The resorbable orthopaedic implant may include a porous structure made of a type I collagen matrix having at least one sheet of naturally occurring extracellular matrix material secured thereto.

The type I collagen matrix may be extracted from a naturally occurring extracellular matrix. In certain embodiments, at least 75% of the collagen fibers of the matrix have an α-helical tertiary structure. In certain embodiments, the porous structure is self-assembled.

In certain embodiments, the porous structure is sandwiched between a number of sheets of a naturally occurring extracellular matrix. In certain embodiments a plurality of sheets of naturally occurring extracellular matrix is positioned on each side of the porous structure. A binding solution containing type I collagen may be disposed between adjacent sheets of the naturally occurring extracellular matrix.

The sheets of naturally occurring extracellular matrix may be sheets of SIS.

A bioactive agent may be incorporated into the implant.

The implant may be formed to include a number of indentations on one side thereof. The implant may be formed to include a corresponding number of protrusions on the other side. The implant may be so formed by use of a die.

The joint surface may be the glenoid surface of a patient. A metallic humeral head may be positioned to bear on the implant.

According to another aspect of the disclosure, a method of performing a surgical joint procedure includes positioning a resorbable orthopaedic implant, having a plurality of indentations formed therein, on a joint surface.

The resorbable implant may include a naturally occurring extracellular matrix.

The implant may include a porous structure having a collagen type I matrix.

In certain embodiments, one or more sheets of a naturally occurring extracellular matrix may be secured to the porous structure.

A bioactive agent may be incorporated into the implant.

The joint surface may be the glenoid surface of a patient. A metallic humeral head may be positioned to bear on the implant.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Definitions

In describing and claiming the invention, the following terminology will be used in accordance with the definitions set forth below.

A used herein the term "bioactive agent" includes one or more of the following: chemotactic agents; therapeutic agents (e.g. antibiotics, steroidal and non-steroidal analgesics and anti-inflammatories, anti-rejection agents such as immunosuppressants and anti-cancer drugs); various proteins (e.g. short chain peptides, bone morphogenic proteins, glycoprotein and lipoprotein; cell attachment mediators; biologically active ligands; integrin binding sequence; ligands; various growth and/or differentiation agents (e.g. epidermal growth factor, IGF-I, IGF-II, TGF-β I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; TGFβ superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids, steroidal and non-steroidal hormones such as vitamin D, ecosanoinds, immuno modulators such as IL10, IL4 and IL12, and synthetic anti-inflammatory and immunomodulating agents such as analgesics, p38 regulators, and other regulators of TNFα up and downstream signaling.

As used herein the term "naturally occurring extracellular matrix" is intended to mean any noncellular extracellular matrix material (such as intestinal submucosa), isolated in its native configuration with or without naturally associated cells, that is naturally secreted by cells.

As used herein the term "submucosal matrices" refers to natural extracellular matrices, known to be effective for tissue remodeling, that have been isolated in their native configuration, including submucosa derived from intestinal tissue (autograft, allograft, and xenograft), stomach tissue (autograft, allograft, and xenograft), bladder tissue (autograft, allograft, and xenograft), alimentary tissue (autograft, allograft, and xenograft), respiratory tissue (autograft, allograft, and xenograft) and genital tissue (autograft, allograft, and xenograft).

As used herein the term "collagen type I matrix" refers to a polymer complex that includes collagen fibers, wherein greater than 75% of the collagen fibers have an α-helical tertiary structure.

As used herein the term "cells" refers to eukaryotic cells and absent any further elaboration/characterization, includes one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyruvate, fungicides, antibiotics, etc., in concentrations deemed appropriate for cell type, shipping conditions, etc.

Preparation of Collagen Type I Matrix

In an exemplary embodiment, a self-assembling protein matrix is prepared using a purified collagen type I composition that is prepared from natural materials that have a high collagen content, including naturally occurring extracellular matrices. In an exemplary embodiment, the method for preparing a composition having a high content of collagen type I fibers includes the steps of extracting collagen type I protein from a naturally occurring extracellular matrix, including for example submucosal tissue, by use of an acidic reagent selected from the group consisting of acetic acid, citric acid, or formic acid. The extraction of the collagen type I protein from the natural material is conducted in the absence of detergents or enzymes. In an exemplary embodiment, the starting material is extracted using acetic acid at a pH of about 2 to about 3.5, and the temperature is kept below 20° C. during the extraction procedure.

The starting material may be comminuted by tearing, cutting, grinding, shearing or the like to enhance the extraction of the collagen type I protein from the starting material. In an exemplary embodiment, the starting material is ground in a frozen or freeze-dried state, and in another exemplary embodiment the starting material is homogenized in a high speed (high shear) blender, and dewatering, if necessary, by centrifuging and decanting excess water. The starting material can be comminuted in the presence of the acidic reagent, or the material can be first comminuted and then contacted with the acidic reagent.

In an exemplary embodiment, the starting material is homogenized in the presence of about 0.1 to about 1.0 M acetic acid, and in another exemplary embodiment 0.5 M acetic acid, while the temperature of the homogenate is maintained below 20° C., and typically the homogenate temperature is kept near 4° C., through out the extraction process. The starting tissue may be subjected to repeated cycles of homogenization in the presence of the acidic reagent, with the homogenate being placed on ice in between the homogenization steps.

The collagen type I containing fraction may be recovered by removing the insoluble fractions by, for example, centrifugation and recovery of the supernatant. In an exemplary embodiment, the extracted starting material is subjected to centrifugation at about 3000×g and the supernatant is recovered. However, other separation techniques such as filtration, and other techniques known to the skill practitioner, can be used to recover the soluble fraction.

The extraction procedures described herein produce a composition that is substantially pure collagen type I in its native α-helical structure, with a low amount of other proteinaceous constituents having β-sheet and random coil secondary structures. In exemplary embodiments, the resulting collagen extract contains 75%, 85%, 90%, 95%, 98% or higher collagen type I in its native α-helical structure.

In exemplary embodiments, the starting material used to isolate the high content collagen type I solution is a tissue that initially contains high collagen type I content. For example, placenta and mammalian tails are known to contain large amounts of collagen type I. The starting material may also be a naturally occurring extracellular matrix. Extracellular matrices isolated from various tissues are known to be effective for tissue remodeling, and include, but are not limited to, extracellular matrices isolated from mammalian intestine, stomach, bladder, alimentary, respiratory, and genital submucosa. See, e.g., U.S. Pat. Nos. 4,902,508, 6,171,344, 6,099,567, and 5,554,389, the disclosures of which are hereby incorporated by reference. These tissues include highly conserved collagens, glycoproteins, proteoglycans, and glycosaminoglycans. Additionally, other known extracellular matrices, for example lamina propria and stratum compactum, may also be used as a starting material.

In a specific exemplary embodiment, the staring material is intestine submucosa, more specifically small intestinal submucosa of a warm blooded vertebrate. For example, the material may include the tunica submucosa along with the lamina muscularis mucosa and the stratum compactum of a segment of intestine, with such layers being delaminated from the tunica muscularis and the luminal portion of the tunica mucosa of the segment. Such a material is referred to herein as small intestinal submucosa (SIS). In an exemplary embodiment, the intestinal submucosa includes the tunica submucosa along with basilar portions of the tunica mucosa of a segment of intestinal tissue of a warm-blooded vertebrate. While porcine SIS is widely used, it will be appreciated that intestinal submucosa may be obtained from other animal sources, including cattle, sheep, and other warm-blooded mammals.

The preparation of SIS from a segment of small intestine is detailed in U.S. Pat. No. 4,902,508, the disclosure of which is expressly incorporated herein by reference. A segment of intestine is first subjected to abrasion using a longitudinal wiping motion to remove both the outer layers (particularly the tunica serosa and the tunica muscularis) and the inner layers (the luminal portions of the tunica mucosa). Typically, the SIS is rinsed with saline and optionally stored in a hydrated or dehydrated state until use. Currently, there are multiple patents and publications that describe in detail the characteristics and properties of intestinal submucosa (SIS). See, for example, U.S. Pat. Nos. 4,352,463, 4,902,508, 4,956,178, 5,281,422, 5,372,821, 5,445,833, 5,516,533, 5,573,784, 5,641,518, 5,645,860, 5,668,288, 5,695,998, 5,711,969, 5,730,933, 5,733,868, 5,753,267, 5,755,791, 5,762,966, 5,788,625, 5,866,414, 5,885,619, 5,922,028, 6,056,777, and WO 97/37613, the disclosures of which are incorporated herein by reference. SIS, in various forms, is commercially available from Cook Biotech Incorporated (Bloomington, Ind.).

In a more specific exemplary embodiment, an intestinal submucosa matrix (e.g., SIS) is used as the starting material, and the material is comminuted by tearing, cutting, grinding, shearing and the like in the presence of an acidic reagent selected from the group consisting of acetic acid, citric acid, and formic acid. In a specific implementation of this exemplary embodiment, the acidic reagent is acetic acid. The intestinal submucosa is ground in a frozen or freeze-dried state to prepare a comminuted form of SIS. Alternatively, comminuted SIS can also be obtained by subjecting a suspension of pieces of the submucosa to treatment in a high speed (high shear) blender, and dewatering, if necessary, by centrifuging and decanting excess water.

The material extracted from SIS (herein referred to as SISH) is mostly composed of collagen type I. This material has been found to be stable in solution at 4° C. for weeks.

The collagenous extracts allow collagen type I matrices to be formed, with such matrices being stable in the presence of acidic solutions. Furthermore, the matrix can be prepared to include bioactive agents or cells and thus it can function as a delivery system. Self-assembly of the collagen type I matrix is permitted and encouraged by an increase in the entropy of its environment, which in one exemplary embodiment is done by raising the temperature to above 20° C., but below 40° C., and in one specific exemplary embodiment raising the temperature to about 34° C. to about 38° C. In an even more specific exemplary embodiment, self assembly is induced by raising the temperature of the collagen extract to about 37° C.

Self assembly may be further encouraged by the addition of small amounts of salts, such as ammonium sulfate solution, sodium phosphate solution, phosphate buffered saline (PBS) solution, or NaCl solution or a combination thereof. The addition of small amounts of salts speeds the formation of the collagenous matrix without significantly impacting the desirable properties of the formed matrix. In an exemplary embodiment, the salt is ammonium sulfate or sodium phosphate or a combination of the two. Ammonium sulfate or sodium phosphate may be added to the collagen extract in final concentration of about 1 mM to about 100 mM. In one exemplary embodiment, the salt used is ammonium sulfate, and is added to a final concentration of about 0.3 mM to about 90 mM. In a more specific exemplary embodiment, ammonium sulfate is added to a final concentration of about 3.0 mM to about 30 mM.

In an exemplary embodiment, a method of assembling a collagen type I matrix may include the steps of applying a composition having a collagen type I solution to a surface, with the collagen type I solution having been prepared by extracting a naturally occurring extracellular matrix with acetic acid at a pH of about 2 to about 3.5. A salt solution is then contacted with the collagen type I solution to induce collagen type I self assembly resulting in a collagen type I matrix formed on the surface. In an exemplary embodiment, the collagen composition and the salt solution are combined to form a mixture, and the mixture is applied to the surface.

Various bioactive agents or cells may be added to the collagen/salt mixture before the mixture has assembled into the collagen type I matrix. Alternatively, the bioactive agent or cells may be adhered to the fibers of the collagen type I matrix after self assembly. In an exemplary embodiment, the bioactive agent is a growth factor. In this case, the matrix may be used as a delivery vehicle for delivering compounds and/or cells to a specific location.

The bioactive agent may be adsorbed onto a formed collagen matrix. Alternatively, the bioactive agent may be mixed with the collagen extract prior to self assembly, in which case induction of self assembly entraps the bioactive agent within the matrix. The approach taken depends on the molecule to be used, its hydrophobicity, structure, size, concentration and ability to interact with collagen. In embodiments where the bioactive agent is mixed with the components prior to self assembly, the composition containing the bioactive agent may be premixed with the salt solution, premixed with the collagen solution in acetic acid, or the three solutions may be simultaneously mixed together.

The properties of the resulting self assembled collagenous matrix may be altered by modifying the concentration of the collagenous solution or the salt concentration. In an exemplary embodiment, the concentration of collagen ranges from about 0.05 mg/ml to about 1.5 mg/ml, with higher concentration of collagen giving rise to material having higher tensile strength.

As a drug delivery system, the collagen type I matrices may be used to design structural systems that can be made to conform to the geometry of the anatomical site where the drug is to be delivered. Furthermore, as structural scaffolds, the material can be used to engineer macromolecular complexes suitable to support the bulk of the mechanical demands of the environment in which they are implanted.

Additional examples and embodiments which may be used to fabricate a collagen type I matrix for use with the concepts of the present disclosure are disclosed in pending U.S. patent application Ser. No. 11/022,517 which is owned by the same assignee as the present application and which is hereby incorporated by reference.

Implant Fabrication

Referring now to FIGS. 1-5, there is shown a resorbable orthopaedic implant 10. The implant 10 may be used to resurface a joint of a patient. For example, the implant 10 may be positioned in the glenoid cavity 12 of a patient's shoulder joint 14. As such, the implant 10 provides a scaffold for the regeneration of the articulating soft tissue surface (i.e., the cartilage of the glenoid cavity). The implant 10 may be used in conjunction with a humeral prosthesis. It should be appreciated that although the concepts discussed in relation to FIGS. 1-5 are herein exemplarily described in regard to an implant for use in the performance of a shoulder procedure, such concepts may be utilized in conjunction with an implant for use in other orthopaedic procedures. For example, such concepts may be utilized in the construction of an implant for implantation into the hip or other joint locations.

Figure 4:
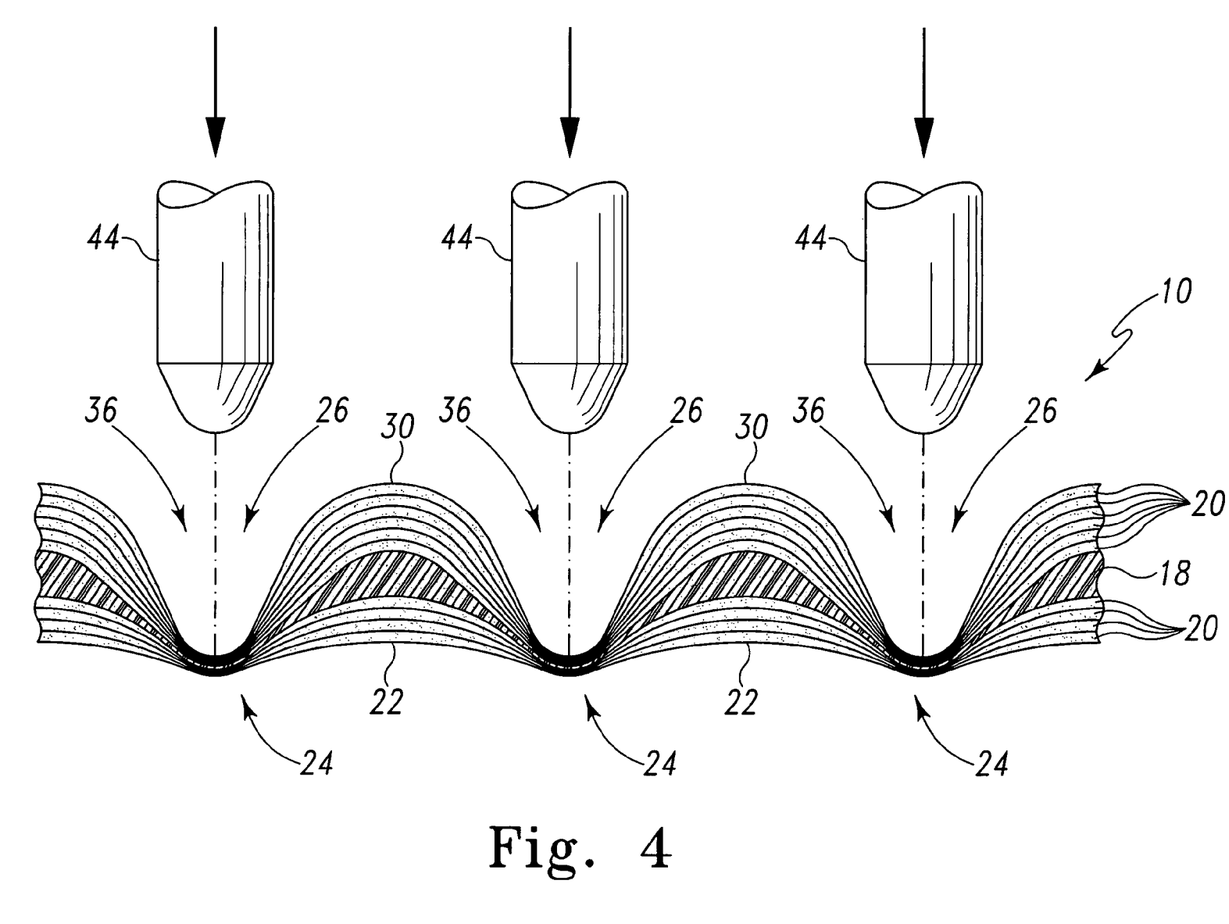
FIG. 4 is a diagrammatic cross sectional view showing the die pins of the die of FIG. 2 and the glenoid implant of FIG. 1.
Figure 5:
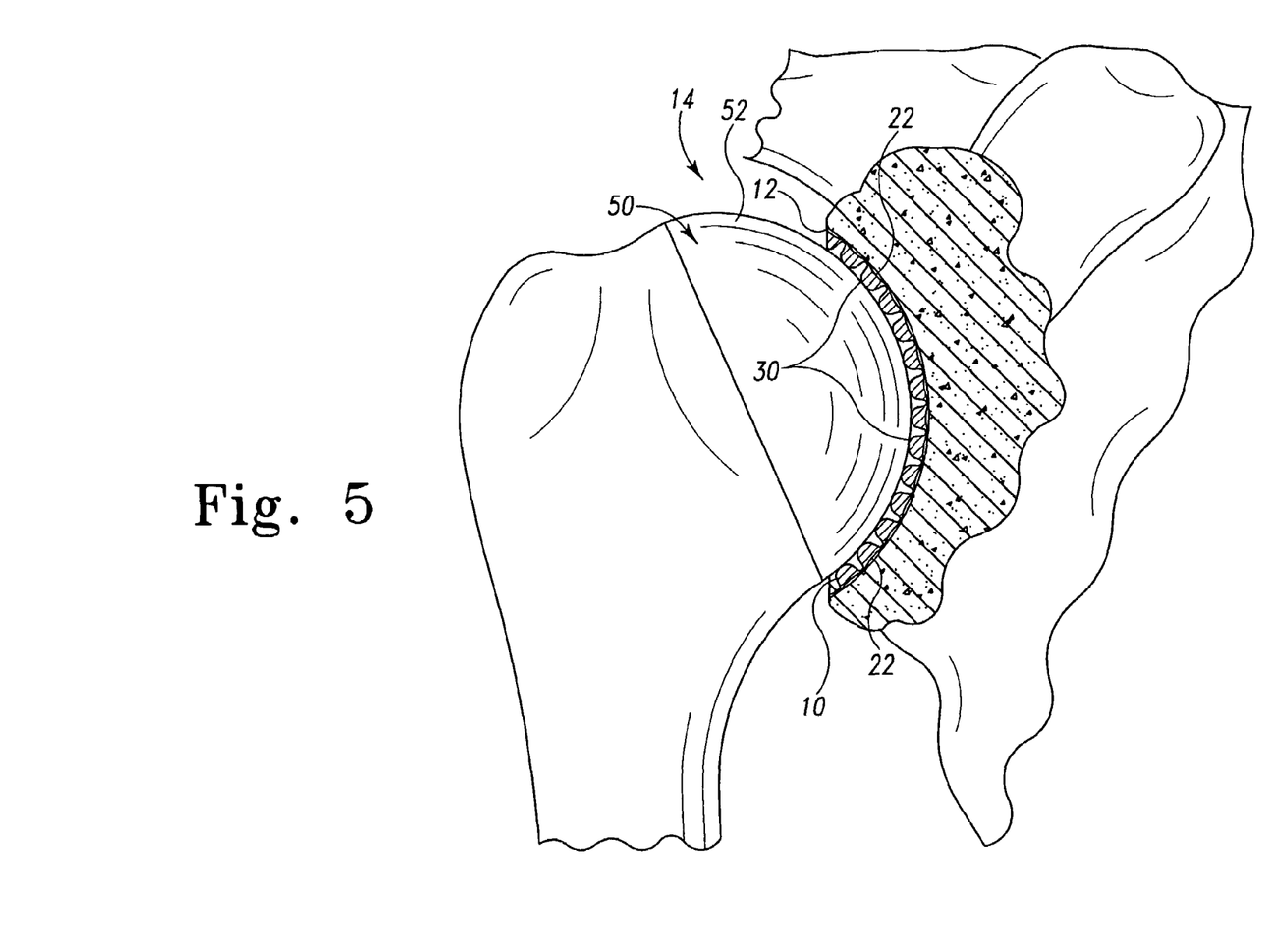
FIG. 5 is a side view showing the glenoid implant of FIG. 1 positioned in the glenoid cavity of the scapula with a prosthetic humeral head bearing thereon, note that a portion of the scapula is shown in cross section for clarity of description.

In one exemplary embodiment, the implant 10 includes a porous structure 18, which will be referred to herein as a sponge, having a number of sheets 20 of naturally occurring extracellular matrix material secured to it. In exemplary embodiments, the sponge 18 is sandwiched between the sheets 20 of naturally occurring extracellular matrix material. Any number of sheets 20 may be used on either side of the sponge 18. Different numbers of sheets 20 may be used on each side of the sponge 18. For example, as shown in FIG. 4, a fewer number of sheets 20 may be used on the side of the implant that is placed in contact with the glenoid 12.

Various bioactive agents and/or cells may be incorporated into or secured to the sponge 18 and/or sheets 20.

A binding agent may be positioned between the sponge 18 and the sheets 20 and/or between each of the sheets 20. The binding agent may be embodied as a solution which enhances the adhesion of the sheets 20 to one another and/or the sponge 18. One exemplary binding agent is a solution containing collagen type I.

The sponge 18 may be fabricated from collagen type I in any of the manners described above. For example, a collagen type I solution may be self assembled into a three dimensional sponge. The collagen type I solution may be extracted from a naturally occurring extracellular matrix. In an exemplary embodiment, the naturally occurring extracellular matrix may be a submucosal matrix such as SIS.

The sheets 20 may be embodied as sheets of any type of a naturally occurring extracellular matrix. The sheets 20 may be sheets of a submucosal matrix such as SIS. In an exemplary embodiment, the sheets 20 are embodied as sheets of clean, disinfected porcine SIS material that were obtained as described in U.S. Pat. Nos. 4,902,508 and 4,956,178.

Figure 1:
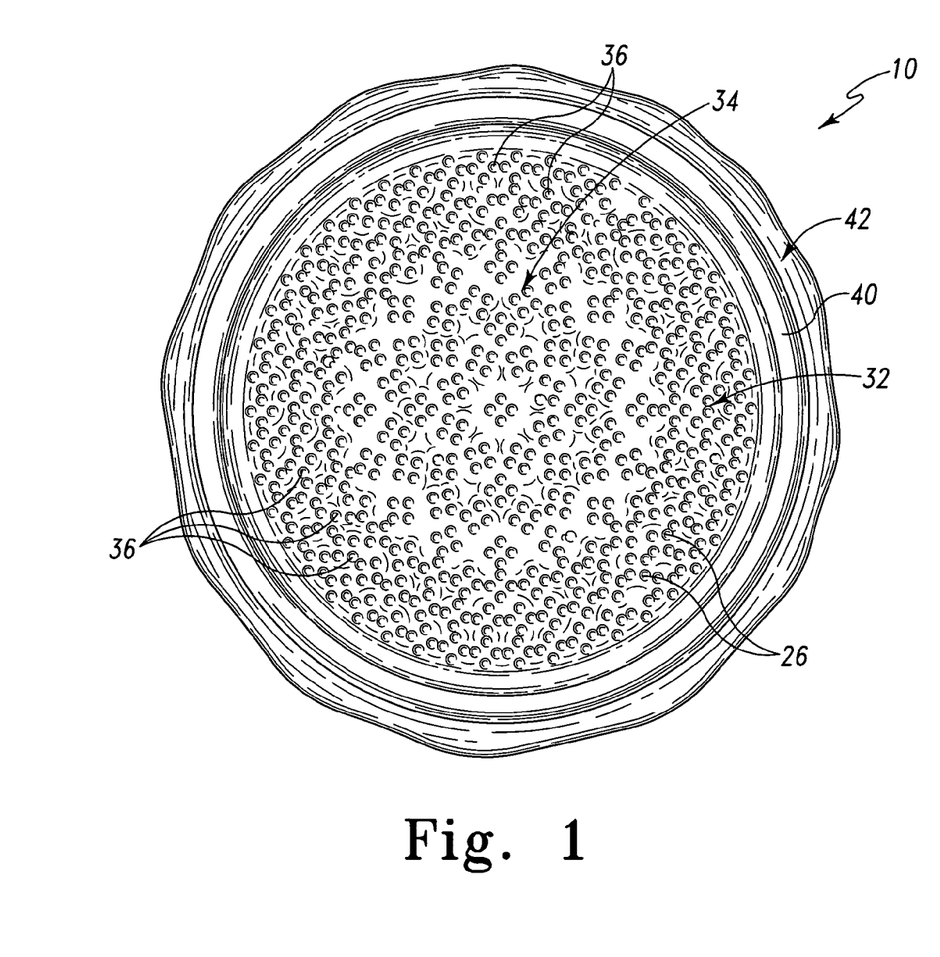
FIG. 1 is a plan view of a glenoid implant.
Figure 2:
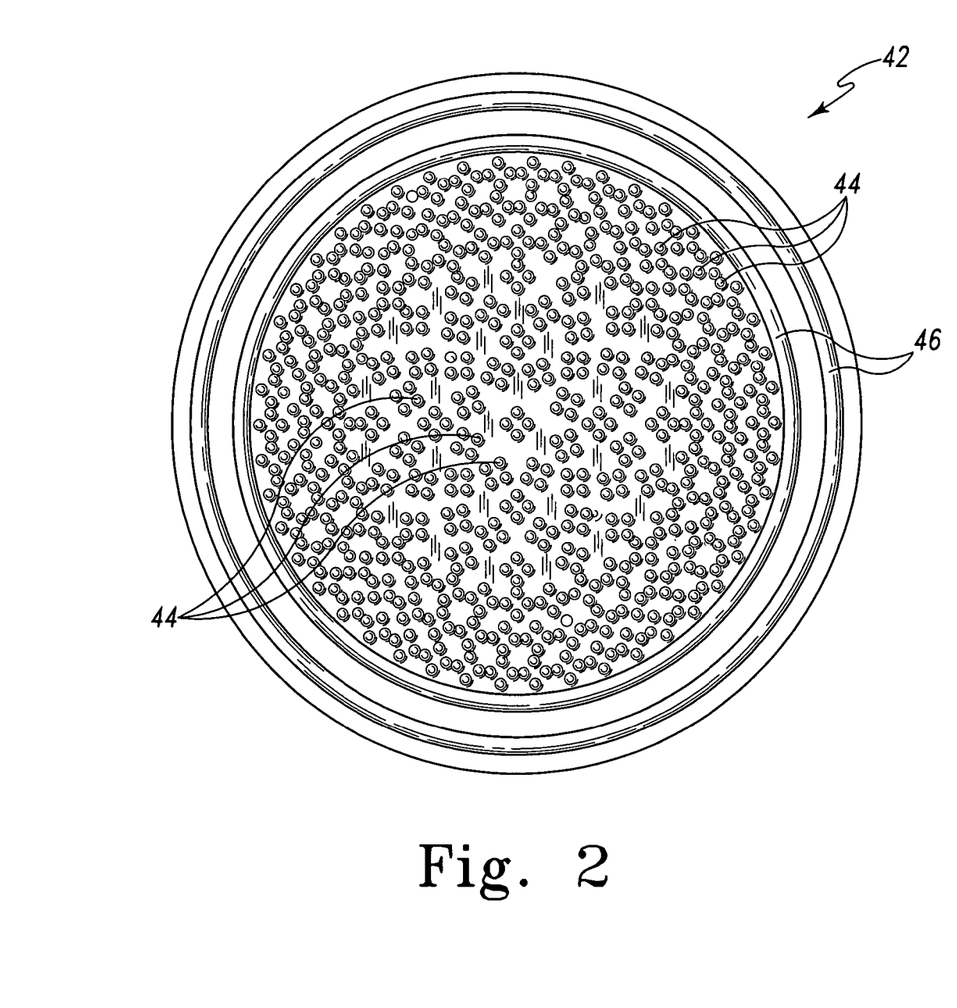
FIG. 2 is a plan view of a die.
Figure 3:
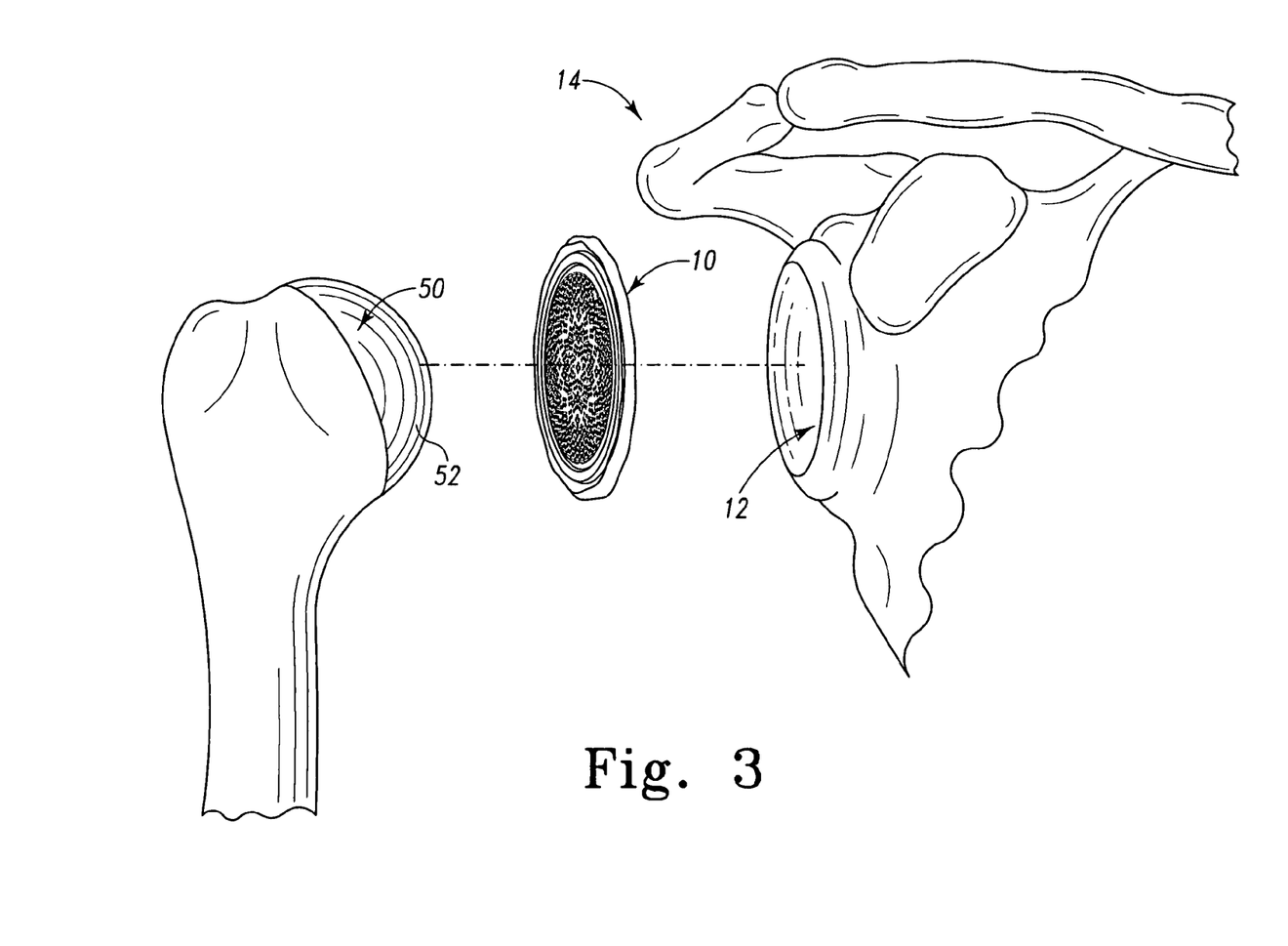
FIG. 3 is an exploded perspective view of a humeral component, the glenoid implant of FIG. 1, and the scapula.

As shown in FIGS. 1, 2, and 4, the implant 10 may be pressed together to secure the layers thereof together. A number of press points 36 are created where the layers of the implant 10 are compressed together by the pins 44 of a die 42 (see FIGS. 2 and 4). Creation of the press points 36 with the individual pins 44 of the die 42 creates adhesion of the layers which reduces, if not prevents delamination, of the implant 10 during normal wear. Use of the die 42 creates a number of indentations 26 in an outer surface 30 of the implant 10. As shown in greater detail in FIG. 4, a number of protrusions 24 may be formed in the opposite, outer surface 22 of the implant 10. By virtue of the forming process (e.g., die pressing), each of the indentations 26 corresponds in location with each of the protrusions 24. It should be appreciated that, based on the type of backing used during the die process, the protrusions 24 may not be formed in the implant 10. In such a case, the outer surface 22 would be relatively flat.

The press points 36 may be arranged in any orientation relative to one another. For example, as shown in FIG. 1, the press points 36 may be arranged relative to one another to form a number of individual diamond shapes. Such a configuration allows the implant 10 to stretch in the radial direction away from its center point. In such a way, the implant 10 is resistant to shearing during translation of the humeral head thereon during normal movement of the shoulder joint. Moreover, shear forces exerted on the implant 10 are greater near the outer periphery of the implant 10. As such, a greater number (and a greater concentration) of the diamond-shaped clusters of the press points 36 are located in an outer radial area 32 of the implant 10 as opposed to the inner radial area 34 of the implant 10. In such a way, greater shear resistance is provided to the outer radial area 32 where greater shear forces are encountered during translation of the humeral head on the implant during normal movement of the shoulder joint.

As shown in FIG. 1, a ring 40 is formed near the outer peripheral edge 42 of the implant 10. The ring 40 seals the edges of the implant 10. A pair of ring-shaped ridges 46 in the die 42 form the ring 40.

Although one exemplary embodiment of the die 42 and the resulating configuration of the implant 10 is shown in FIGS. 1 and 2, it should be appreciated that numerous other configurations may be used. For example, any number and arrangement of press points 36 may be used. In addition to the diamond-shaped configuration shown in FIGS. 1 and 2, the press points 36 may be arranged in any configuration. Fewer or more of the diamond-shaped clusters may be positioned in the inner radial area 34 and the outer radial area 32. Any configuration of the ring 40 may be used. For example, the ring 40 may be embodied as a number of discreet segments instead of a continuous ring. More than one ring 40 may be used. In essence, the pattern of the die 42 may be configured to produce a work tool that fits the needs of a given implant design.

Moreover, in addition to die pressing, other fabrication techniques may be used to form the dimpled pattern in an orthopaedic implant. For example, such a pattern may be molded into the implant.

Yet further, it should also be appreciated that the concepts disclosed herein relating to use of a die for the formation of dimpled patterns on an implant are not limited to any type of resorbable orthopaedic implant. In particular, although numerous examples of implants are disclosed herein (e.g., multiple layer constructs having the sponge 18 and the sheets 20), it should be appreciated that a die may be used to form patterns in other types of implants and, as such, any of the appended claims drawn to the use of a die should not be construed to imply any particular type of implant construction unless specifically recited in the particular claim.

Implant Example

The following describes an exemplary implant fabricated using the concepts disclosed herein.

The sponge was fabricated as a self assembled, three-dimensional matrix using one of the methods described above. In particular, 12-15 ml of 1 mg/ml solution of collagen type I was extracted from SIS and poured into a 6 cm Petri dish. The dish was covered and placed at −70° C. for about an hour. The solution was then lyophilized to completion (e.g., 24-48 hours) to form the sponge.

Thereafter, a number of sheets of SIS were layered, without stretching, over a 2.5" drum. Between each layer, 0.5 ml of the 1 mg/ml collagen type I solution was added as a binding agent. The alternating placement of an SIS sheet and collagen solution was repeated five times (six sheets total), and thereafter the sponge was placed on top of the sheets.

Once the sponge was placed on the six sheets, 1 ml of 1 mg/ml solution of the collagen type I solution was applied to the sponge and a sheet of SIS was placed over the sponge. Thereafter, the construct was completed by adding three more sheets of SIS with 0.5 ml of the 1 mg/ml collagen type I solution being applied between each sheet in a similar manner to as above. As such, the construct included six sheets of SIS below, the sponge, and four sheets of SIS above.

A round piece of foam was placed on a second drum. The construct was then flipped upside down and gently stretched onto the foam. The first drum was then removed and replaced by the die. The first drum was then placed on top of the die. The whole assembly was then clamped together. The whole assembly was then placed at −70° C. for at least four hours and then lyophilized until dry (24-48 hours). The clamps, drums, and die are then removed. The implant was trimmed to remove any flashing and packaged for electron-beam sterilization.

Surgical Implantation

In an exemplary surgical method, the implant 10 is implanted as part of a hemiarthroplasty procedure. In such a procedure, only a humeral component 50 is implanted (as opposed to also implanting a polyethylene glenoid component). In such a case, the glenoid cartilage may be left intact. Alternatively, the glenoid may be reamed to remove the cartilage to produce a bleeding bone bed (such a procedure being referred to as "Ream and Run").

The implant 10 is positioned against the glenoid cartilage or reamed glenoid surface such that a prosthetic head 52 of the humeral component 50 bears on the implant 10. Generally, the prosthetic head 52 is constructed with implant grade metals such as stainless steel, cobalt chrome, titanium, along with combinations and/or alloys thereof. The head 52 may also be constructed with non-metallic materials such as implant-grade polymers or ceramics.

The implant 10 may be arranged in any desired orientation. In one exemplary embodiment in which the implant 10 includes a greater number of sheets 20 of naturally occurring extracellular matrix material on one side of the sponge 18 versus the other, the side with fewer sheets 20 is placed in contact with the glenoid cartilage or reamed glenoid. However, the opposite may be done as well.

Moreover, the implant 10 may be positioned such that the surface 30 having the indentations 26 formed therein faces toward the prosthetic head 52 of the humeral component 50, with the opposite surface 22 of the implant 10 being positioned to contact the glenoid cartilage or the reamed glenoid. However, the opposite may be done as well.

In any implanted orientation, the implant 10 maintains the interpositional space of the joint. In addition, it also promotes healing of the articular cartilage by providing a scaffold for growth factor binding and enrichment, cell attachment, and differentiation. Moreover, use of the implant 10 alleviates pain during use of the shoulder. Use of the implant 10 in such a manner also accelerates the formation (i.e., regeneration) of a resurfacing tissue that is biochemically and physiologically adapted to articulating with a metal surface (i.e., the metal humeral head 52).

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. An orthopaedic implant, comprising:
    a self-assembled porous structure comprising a collagen type I matrix, wherein the self-assembled porous structure contains 75% collagen type I in its native α-helical structure, and
    at least one sheet of naturally occurring submucosal matrix secured to the self-assembled porous structure.

2. The orthopaedic implant of claim 1, wherein:
    the at least one sheet of naturally occurring submucosal matrix comprises a first sheet of naturally occurring submucosal matrix and a second sheet of naturally occurring submucosal matrix, and the self-assembled porous structure is sandwiched between the first sheet of naturally occurring submucosal matrix and the second sheet of naturally occurring submucosal matrix.

3. The orthopaedic implant of claim 2, wherein:

the first sheet of naturally occurring submucosal matrix comprises a sheet of small intestinal submucosa (SIS) and the second sheet of naturally occurring extracellular matrix comprises a sheet of small intestinal submucosa (SIS).

4. The orthopaedic implant of claim 1, wherein:

the at least one sheet of naturally occurring submucosal matrix comprises a first plurality of sheets of naturally occurring submucosal matrix and a second plurality of sheets of naturally occurring submucosal matrix, and the self-assembled porous structure is sandwiched between the first plurality of sheets of naturally occurring submucosal matrix and the second plurality of sheets of naturally occurring submucosal matrix.

5. The orthopaedic implant of claim 4, wherein:

the first plurality of sheets of naturally occurring submucosal matrix comprises a plurality of sheets of SIS, and the second plurality of sheets of naturally occurring submucosal matrix comprises a plurality of sheets of SIS.

6. The orthopaedic implant of claim 1, wherein:

the at least one sheet of naturally occurring submucosal matrix comprises a first number of sheets of naturally occurring submucosal matrix and a second number of sheets of naturally occurring submucosal matrix, the first number of sheets being greater than the second number of sheets, and the self-assembled porous structure is sandwiched between the first number of sheets of naturally occurring submucosal matrix and the second number of sheets of naturally occurring submucosal matrix.

7. The orthopaedic implant of claim 6, wherein:

the first number of sheets of naturally occurring submucosal matrix comprises a number of sheets of SIS, and the second number of sheets of naturally occurring submucosal matrix comprises a number of sheets of SIS.

8. The orthopaedic implant of claim 1, further comprising a plurality of indentations formed in an outer surface of the implant.

9. The orthopaedic implant of claim 1, wherein:

the at least one sheet of naturally occurring submucosal matrix comprises a first number of sheets of naturally occurring submucosal matrix and a second number of sheets of naturally occurring submucosal matrix, the self-assembled porous structure is sandwiched between the first number of sheets of naturally occurring submucosal matrix and the second number of sheets of naturally occurring submucosal matrix, and the first number of sheets of naturally occurring submucosal matrix has a plurality of indentations formed therein.

10. The orthopaedic implant of claim 9, wherein:

the first number of sheets of naturally occurring submucosal matrix comprises a number of sheets of SIS, and the second number of sheets of naturally occurring submucosal matrix comprises a number of sheets of SIS.

11. The orthopaedic implant of claim 1, further comprising a bioactive agent.

12. An orthopaedic device, comprising:

a resorbable orthopaedic implant configured to resurface a joint, the resorbable orthopaedic implant having a self-assembled porous structure comprising a collagen type I matrix, wherein the self-assembled structure contains 75% collagen type I in its native $\alpha$-helical structure, and the resorbable orthopaedic implant has a plurality of indentations on a first surface thereof.

13. The orthopaedic device of claim 12, wherein the resorbable orthopaedic implant has a plurality of protrusions on a second surface thereof at locations corresponding with the locations of the plurality of indentations on the first surface.

14. The orthopaedic implant of claim 12, wherein the resorbable orthopaedic implant comprises a naturally occurring submucosal matrix.

15. The orthopaedic implant of claim 12, wherein the resorbable orthopaedic implant comprises:

at least one sheet of naturally occurring submucosal matrix secured to the self-assembled porous structure.

16. The orthopaedic implant of claim 12, wherein the resorbable orthopaedic implant comprises:

a number of sheets of naturally occurring submucosal matrix sandwiching the self-assembled porous structure.

17. The orthopaedic implant of claim 12, wherein:

the orthopaedic implant comprises an inner radial area and an outer radial area, a first number of the indentations are positioned in the inner radial area, a second, greater number of the indentions are positioned in the outer radial area.

18. The orthopaedic implant of claim 12, further comprising a bioactive agent.

* * * * *